United States Patent [19]

Nishibori et al.

[11] Patent Number: 5,710,347
[45] Date of Patent: Jan. 20, 1998

[54] METHOD OF PRODUCING A HIGH-MELTING POWDER OF 2,2-BIS[4'-(2",3"-DIBROMOPROPOXY)-3',5'-DIBROMOPHENYL]-PROPANE

[75] Inventors: Setsuo Nishibori; Hideaki Ohnishi, both of Shiga; Tsuyoshi Furukawa, Kyoto, all of Japan

[73] Assignee: Dai-Ichi Kogyo Seiyaku Co., Ltd., Kyoto, Japan

[21] Appl. No.: 533,822

[22] Filed: Sep. 26, 1995

[51] Int. Cl.$^6$ .................................. C07C 37/24
[52] U.S. Cl. .......................... 568/725; 568/724
[58] Field of Search .................... 568/725, 724

[56] References Cited

U.S. PATENT DOCUMENTS 4,737,352  4/1988  Owen et al. ..................... 423/122

FOREIGN PATENT DOCUMENTS

| 1803420 | 7/1969 | Germany . |
|---|---|---|
| 48030269 | 9/1973 | Japan . |
| 57-289 | 1/1982 | Japan . |
| 57000289 | 1/1982 | Japan . |

OTHER PUBLICATIONS

Novikov et al; "Tr. Nauls.–Issled. Inst. Osn. Khim." 20, 89–93 (1969).

*Primary Examiner*—Gary Geist
*Assistant Examiner*—Sreeni Padmanabhan
*Attorney, Agent, or Firm*—Jordan and Hamburg

[57] ABSTRACT

This invention relates to a method of producing a high-melting powder of 2,2-bis[4'-(2",3"-dibromopropoxy)-3',5'-dibromophenyl]propane characterized by comprising a step of adding water to a solution of 2,2-bis[4'-(2",3"-dibromopropoxy)-3',5'-dibromophenyl]-propane in an organic solvent in the presence of a surfactant to give a water-in-oil emulsion and a step of removing the organic solvent from the emulsion in the presence of a crystal nucleus to induce crystallization to give an aqueous dispersion of 2,2-bis[4'-(2",3"-dibromopropoxy)-3',5'-dibromophenyl]propane. In accordance with this invention, crystallization is carried out in the state of an emulsion under assistance of a surfactant so that an ordinary stirrer can be used in production without resort to any special high-shear stirring equipment. Moreover, since a high-melting grade of 2,2-bis[4'-(2",3"-dibromopropoxy)-3',5'-dibromophenyl] propane is obtained as an aqueous dispersion, workability and safety in the subsequent processing are improved.

5 Claims, No Drawings

METHOD OF PRODUCING A HIGH-MELTING POWDER OF 2,2-BIS[4'-(2",3"-DIBROMOPROPOXY)-3',5'-DIBROMOPHENYL]-PROPANE

BACKGROUND OF THE INVENTION

This invention relates to a method of producing a high-melting powder of 2,2-bis[4'-(2",3"-dibromopropoxy)-3',5'-dibromophenyl]propane from a solution of the compound in an organic solvent.

It is known that 2,2-bis[4'-(2",3"-dibromopropoxy)-3',5'-dibromophenyl]propane (hereinafter sometimes referred to briefly as BDBP-TBA), when added to various resins, improves the fire resistance of the resins.

BDBP-TBA as such can be easily produced as a solution of high purity typically by a process in which tetrabromo-bisphenol A is converted to a diallyl ether which is then brominated in an inert solvent. Concentrating this solution yields a resinous solid having a melting point of 40°–50° C. However, it takes many hours to achieve solidification and it is also difficult to produce a granular, powdery or flaky solid by means of a chiller or a flaker. Furthermore, because of its low melting point, this resinous solid tends to undergo fusion and solidification in storage or stick to the equipment during use. In view of this disadvantage, development of a high-melting product has been demanded.

As a means for overcoming the above disadvantage, it is described in Japanese Patent Publication No. 57-289 that a BDBP-TBA product with a melting point of 80°–100° C. can be produced by the procedure of adding either a non-solvent or a poor solvent to a solution of BDBP-TBA in a good solvent and stirring the mixture with a shear force.

However, the melting point of BDBP-TBA that can be obtained by the above procedure described in the prior art literature is 80°–100° C. and, moreover, the highest melting point actually mentioned in the production examples is 92° C. Moreover, since, in this prior art, a solution in a good solvent such as a halogenated hydrocarbon or an aromatic hydrocarbon is extracted with a poor solvent such as an alcohol, reclaiming the solvents for reuse requires a distillation or other fractionation procedure and, therefore, the technology is not reasonably acceptable. Moreover, this prior technology requires a special stirrer such as a twin-screw kneader or a homomixer but this requirement is onerous both equipment-wise and cost-wise.

SUMMARY OF THE INVENTION

This invention has for its object to provide a method of producing a high-melting grade of BDBP-TBA, which method permits reuse of the solvent as recovered and use of ordinary stirring equipment, not any special stirring equipment.

This invention, therefore, is concerned with a method of producing a high-melting powder of 2,2-bis[4'-(2",3"-dibromopropoxy)-3',5'-dibromophenyl]propane which comprises a step of adding water to a solution of 2,2-bis[4'-(2", 3"-dibromopropoxy)-3',5'-dibromophenyl]propane in an organic solvent in the presence of a surfactant to give a water-in-oil emulsion and a subsequent step of removing the organic solvent in the presence of a crystal nucleus to give an aqueous dispersion of high-melting 2,2-bis[4'-(2",3"-dibromopropoxy)-3',5'-dibromophenyl]propane crystals.

The mechanism of formation of a high-melting powder of BDBP-TBA in this invention seems to be as follows. Thus, as water is added to a solution of BDBP-TBA in an organic solvent in the presence of a surfactant, the water is emulsified into the organic solvent containing BDBP-TBA to give a water-in-oil emulsion. As the continuous oil phase containing BDBP-TBA is concentrated with progressive removal of the solvent under maintenance of the emulsion state, a concentrated BDBP-TBA solution extremely small in thickness is obtained, and crystallization takes place as the concentration of BDBP-TBA and the temperature become ripe for crystallization. If a crystal nucleus such as a BDBP-TBA powder or a water-insoluble metal hydroxide or oxide is concomitantly present in this system, this crystallization takes place at a high speed. With the progress of crystallization, the emulsion is disrupted and the water forms a continuous phase so that crystals of BDBP-TBA are obtained in the form of an aqueous dispersion.

In accordance with this invention, in which crystallization is caused to take place under the maintenance of an emulsion by a surfactant, no special stirrer of the shear type is required but the objective product can be obtained with an ordinary stirrer. Moreover, there occurs no intermingling of solvents but the organic solvent is distillatively recovered in good yield so that it can be reused after a procedure as simple as phasic separation from water. In addition, since BDBP-TBA is obtained as an aqueous dispersion, its handling in the post-crystallization procedures such as dehydrative filtration and drying is facilitated and made safer. Thus, the invention provides a simple, economic, safe and very reasonable method for producing a high-melting grade of BDBP-TBA.

DETAILED DESCRIPTION OF THE PREFERRED EMBODIMENTS

The starting material BDBP-TBA to be dissolved in an organic solvent in the practice of this invention is preferably of a purity not less than 85% in terms of the liquid chromatographic peak area ratio calculated from UV detection data at 254 nm. If the purity of the starting material is less than 85%, the product BDBP-TBA tends to have a low melting point. As to the organic solvent solution of BDBP-TBA, it may be a solution of a low-melting resinous grade of BDBP-TBA in an organic solvent or a solution available from the bromination step of the precursor 2,2-bis(4'-allyloxy-3',5'-dibromophenyl)propane in the reaction-inert organic solvent.

The organic solvent for use in this invention is a solvent substantially insoluble in water, thus including but not limited to halogenated hydrocarbons such as methylene chloride, chloroform, carbon tetrachloride, dichloroethane, ethylidene chloride, 1,2-dichloroethylene, 1,1,1-trichloroethane, trichloroethylene, etc. and aromatic hydrocarbons such as benzene, toluene, xylene, chlorobenzene, etc. In the method of this invention, however, since BDBP-TBA does not crystallize at any temperature over 80° C., the crystallizing temperature must not be higher than 80° C., although the temperature for solvent removal may be higher than 80° C. Thus, while even a high-boiling organic solvent can be recovered at a temperature below 80° C. by conducting distillation under reduced pressure, the use of an organic solvent having a boiling point higher than the boiling point of water or an organic solvent containing much water to form an azeotropic system is undesirable in view of the possible disruption of the water-in-oil emulsion or from economic points of view. Moreover, when this invention is carried into practice immediately following the bromination reaction, BDBP-TBA is available in the form of a solution in an organic solvent inert to bromine and, therefore, it is a reasonable choice to subject the solution as it is to the treatment of this invention without changing the organic solvent. Therefore, the preferred solvent for use in this invention is a halogenated hydrocarbon such as methylene chloride, chloroform, carbon tetrachloride, dichloroethane, ethylidene chloride and 1,2-dichloroethylene, among others.

The function of the surfactant for use in this invention is to insure formation of a water-in-oil emulsion and can be any of cationic, anionic and nonionic surfactants. However, a large majority of cationic surfactants contain nitrogen and, therefore, present coloration and odor problems if BDBP-TBA contains their residues. Thus, these surfactants are not recommended.

As to anionic surfactants, surfactants of the sulfate, sulfonate, sulfosuccinate, fatty acid and phosphoric ester types can be mentioned. However, since the metal salts or amine salts are strongly ionic, they tend to disrupt the water-in-oil emulsion in the course of solvent removal or an inversion of emulsion prior to crystallization so that the product BDBP-TBA may become increased in particle diameter to give a greater on-sieve percentage, thus detracting from the yield of the product. From these considerations, acidic phosphoric ester surfactants in particular are preferred. These surfactants can be used alone or in combination with other anionic surfactants of the sulfate, sulfonate, sulfosuccinate, fatty acid, phosphoric ester metal salt or amine salt type and/or nonionic surfactants of the ethoxylate type. The acidic phosphoric ester surfactants have the additional advantage that when the system is neutralized after formation of an aqueous dispersion of BDBP-TBA particles, its water-solubility is increased and its adsorption on the BDBP-TBA particles in the filtration step is decreased, thus facilitating the rinsing procedure.

The acidic phosphoric ester surfactant that can be used includes unneutralized phosphoric esters of the substituted phenol type which can be obtained by adding an average of 1–30 mols of ethylene oxide (EO) per mol of a substituted phenol, such as nonylphenol, dinonylphenol, octylphenol, dioctylphenol, styrenated phenol, distyrenated phenol, tristyrenated phenol, etc., with the aid of an alkali metal or tertiary amine catalyst to give a substituted phenol ethoxylate and reacting the ethoxylate with a phosphorylating agent such as phosphoric acid, polyphosphoric acid, phosphoric anhydride, phosphorus oxychloride, etc. These are mixtures composed predominantly of phosphoric monoesters and/or phosphoric diesters and containing small proportions of phosphoric triester, pyrophosphoric ester, inorganic phosphoric acid, etc. There can also be mentioned unneutralized phosphoric esters of the higher alcohol type which are obtainable by reacting higher alcohols or higher alcohol ethoxylates, which are obtainable by adding an average of 1–30 mols of ethylene oxide per mole of higher alcohols with the aid of an alkali metal or tertiary amine catalyst, with a phosphorylating agent such as phosphoric acid, polyphosphoric acid, phosphoric anhydride, phosphorus oxychloride, etc. The higher alcohols that can be used for this purpose are saturated or unsaturated natural or synthetic alcohols containing 8–18 carbon atoms. Natural alcohols are mixtures of alcohols derived from vegetable oils or animal fats or simple substances obtained by elaborate fractional distillation of them. Thus, plant-derived alcohols such as coconut alcohol, palm alcohol, palm kernel alcohol, etc., animal-derived alcohols such as tallow alcohol, hydrogenated tallow alcohol, etc., and such alcohols as n-octyl alcohol, n-decyl alcohol, lauryl alcohol, myristyl alcohol, palmityl alcohol, stearyl alcohol, oleyl alcohol and linoleyl alcohol, all of which are obtainable by fractional distillation of the above-mentioned mixture alcohols, can be typically mentioned. Synthetic alcohols may for example be oxoalcohols or alcohols obtainable by condensation reaction of aldehydes, such as 2-ethylhexanol. Specifically, Dobanol 23, Dobanol 25 and Dobanol 45 manufactured by Shell Chemical Co., Diadol 11, Diadol 115L, Diadol 115H, Diadol 13 and Diadol 135 manufactured by Mitsubishi Kasei Corporation, Oxocol 1213, Oxocol 1215 and Oxocol 1415 manufactured by Kyowa Hakko Kogyo Co., and nonyl alcohol, undecyl alcohol, tridecyl alcohol and pentadecyl alcohol which can be obtained by fractional distillation of said alcohols can be mentioned. Moreover, secondary alcohols obtainable by oxidation of paraffin are commercially available in ethoxylated forms and, as examples, Softanol 30, Softanol 50, Softanol 70, Softanol 90 and Softanol 120 manufactured by Nippon Shokubai Co. can be mentioned. The phosphoric ester surfactants mentioned above can be used singly or in combination.

Nonionic surfactants of the ethoxylate type are substituted phenol ethoxylates and higher alcohol ethoxylates, containing an average of 40–90 weight % of ethylene oxide in each surfactant molecule. They may be mixtures of two or more species. Among typical substituted phenols are nonylphenol, dinonylphenol, octylphenol, dioctylphenol, dodecylphenol, didodecylphenol, styrenated phenol, distyrenated phenol, and tristyrenated phenol, and nonionic surfactants of the ethoxylated type can be obtained by adding an average of 40–90 weight % of ethylene oxide to these substituted phenols with the aid of, for example, an alkali metal or tertiary amine catalyst. The higher alcohols that can be used are saturated or unsaturated natural and synthetic alcohols containing 8–18 carbon atoms. Natural alcohols are mixture alcohols derived from vegetable oils or animal fats or simple substances obtainable by elaborate fractional distillation of them. As examples, alcohols of vegetable origin such as coconut alcohol, palm alcohol, palm kernel alcohol, etc., alcohols of animal origin such as tallow alcohol, hydrogenated tallow alcohol, etc., and n-octyl alcohol, n-decyl alcohol, lauryl alcohol, myristyl alcohol, palmityl alcohol, stearyl alcohol, oleyl alcohol and linoleyl alcohol which are obtainable by fractional distillation of such mixture alcohols can be mentioned. Examples of synthetic alcohols may include oxoalcohols, secondary alcohols which can be obtained by oxidation of paraffin, and alcohols obtainable by condensation of aldehydes, such as 2-ethylhexanol. Specifically, Dobanol 23, Dobanol 25 and Dobanol 45 manufactured by Shell Chemical Co., Diadol 11, Diadol 115L, Diadol 115H, Diadol 13 and Diadol 135 manufactured by Mitsubishi Kasei Corporation, Oxocol 1213, Oxocol 1215 and Oxocol 1415 manufactured by Kyowa Hakko Kogyo Co., nonyl alcohol, undecyl alcohol, tridecyl alcohol and pentadecyl alcohol which can be obtained by fractional distillation of the above alcohols can be mentioned. By adding an average of 40–90 weight % of ethylene oxide to these higher alcohols with the aid of, for example, an alkali metal or tertiary amine catalyst, nonionic surfactants of the ethoxylate type which can be used in this invention can be obtained. Softanol 50, Softanol 70, Softanol 90 and Softanol 120, all manufactured by Nippon Shokubai Co., which are ethoxylation products of secondary alcohols obtained by oxidation of paraffin can also be used in combination with said acidic phosphoric ester surfactants.

The preferred total level of addition of surfactants is 0.05–5 weight % based on BDBP-TBA. In the case of acidic phosphoric ester surfactants, a proportion of 0.05–3 weight % is particularly recommendable. If the proportion of acidic phosphoric ester surfactants is less than 0.05 weight %, a water-in-oil emulsion cannot be stably maintained so that it is difficult to obtain a powdery BDBP-TBA. If said limit of 3 weight % is exceeded, no commensurate increase in the effect can be realized. The use of an acidic phosphoric ester surfactant in combination with a different type of anionic surfactant and/or an ethoxylate type nonionic surfactant may produce the effect of depressing the viscosity of the water-in-oil emulsion immediately preceding crystallization of BDBP-TBA so that the burden on the stirrer can be alleviated. However, when the total amount of surfactants exceeds 5 weight %, no commensurate increase in the effect can be obtained and rather the COD of the waste water is increased to impose a burden on waste water treatment, thus detracting from the economics of operation.

The amount of water necessary for formation of a water-in-oil emulsion is 20–100 weight % relative to BDBP-TBA and the method and timing of addition of water are not critical only if a water-in-oil emulsion is formed before BDBP-TBA begins to crystallize. Therefore, the whole amount of water can be added before the beginning of recovery of the organic solvent or at an optional stage preceding the onset of crystallization after beginning of recovery of the organic solvent, either in bolus, in installments, or continuously. However, if BDBP-TBA is allowed to crystallize from a water-in-oil emulsion system which is deficient in water, desruption of the emulsion after crystallization may not be satisfactorily accomplished so that dispersion of crystals will be insufficient. If this is the case, a further amount of water can be added so as to achieve a complete dispersion of crystals. It is also possible to add water for the purpose of adjusting the viscosity of the aqueous dispersion but the excessive use of water is not economical, of course, because the burden of waste water disposal is increased. Therefore, the total amount of water in the aqueous dispersion is preferably controlled within the range of 50–200 weight % based on BDBP-TBA.

The crystallizing procedure of this invention includes an application of the phase-inversion emulsification technique which has been conventionally used for emulsifying oils in water and involves crystallization of BDBP-TBA from a water-in-oil emulsion prior to phase inversion. However, if the phase inversion takes place before crystallization, a stable oil-in-water emulsion is produced to considerably interfere with a further removal of the solvent. Moreover, the crystallization of BDBP-TBA is not completed in a short time regardless of temperature and the emulsion is disrupted on cooling with the result that BDBP-TBA particles conglomerate to form paste-like masses and, hence, the desired powder cannot be obtained. It is, therefore, necessary that crystallization be initiated as soon as BDBP-TBA has become ready to crystallize in the course of removal of the organic solvent and be completed in a relatively short time. This requirement can be met by adding a crystal nucleus. A suitable crystal nucleus is a high-melting powder of BDBP-TBA. It is necessary that 0.001–10 weight % of the crystal nucleus relative to BDBP-TBA be added before commencement of solvent recovery and/or in the course of solvent recovery before BDBP-TBA crystallizes. However, where the starting BDBP-TBA has not been thoroughly dissolved in the organic solvent but some crystals of BDBP-TBA remain in the organic solvent solution, the solution can be directly treated without addition of a crystal nucleus.

Meanwhile, when a resin is to be rendered flame-retardant with a halogen type flame retardant, it is common practice to use antimony oxide concomitantly in expectation of a synergistic effect. Since antimony oxide does not detract from the utility of the resin in fire retardation uses even if it finds its way into the substrate resin as a contaminant, antimony oxide can be utilized as said crystal nucleus for such applications. Similarly, metal hydroxides and oxides which are insoluble in water and organic solvents, such as aluminum hydroxide, magnesium hydroxide, silica, alumina, magnesium oxide, etc. can also be used as said crystal nucleus.

The BDBP-TBA crystals in an aqueous dispersion obtained by the above technique do not melt or fuse even at a temperature near 80° C. and, therefore, a further removal of the solvent can be carried out. Moreover, the dry powder of BDBP-TBA as a final product can be manufactured by performing, following the above process, a step of neutralizing the aqueous dispersion (where the acidic phosphoric ester surfactant is used), a step of filtrative collection of BDBP-TBA crystals, a rinsing step, a drying step, and, where necessary, a crushing/classifying step for size selection. The melting point of the resulting dry BDBP-TBA powder as determined with an automatic melting point measuring instrument (Mettler) at a temperature incremental rate of 2° C./min. is not lower than 100° C., thus meeting the object of this invention.

In accordance with this invention, crystallization is carried out in an emulsion state with the aid of a surfactant so that the objective product can be produced with an ordinary stirring means without requiring a special high-shear stirring machine. Moreover, since a high-melting BDBP-TBA is obtained as an aqueous dispersion, workability and safety in the subsequent production steps are improved. In addition, since the solvent used is not intermingled but is recovered as it is in high yield by distillation, it can be reused by a procedure as simple as phasic separation.

The following examples are intended to describe this invention in further detail without defining the scope of the invention. In the examples, all "parts" and "%" are by weight and all melting point values are those measured with an automatic melting point measuring instrument.

EXAMPLE 1

A 500 ml glass flask equipped with an anchor-shaped stirring blade was charged with 200 parts of BDBP-TBA of 87% purity having a melting point of 42° C. and 200 parts of methylene chloride and the BDBP-TBA was thoroughly dissolved. The flask was further charged with 200 parts of water, 1 part of nonylphenol ethoxylate (an average of 9 mols of EO added) phosphate, and, as a crystal nucleus, 10 parts of a BDBP-TBA powder having a melting point of 114° C. With the stirrer being driven at 300 rpm, the temperature was increased for distillative recovery of methylene chloride. When the concentration of BDBP-TBA in the methylene chloride phase as calculated from the recovery rate of methylene chloride reached 92% and the temperature became 60° C., crystallization took place, promptly giving rise to an aqueous dispersion. As the temperature was further increased to 70° C. for distillative recovery of methylene chloride, the recovery rate of methylene chloride reached 97%. This aqueous dispersion was cooled to ≦25° C., neutralized with sodium hydroxide and passed through a 1 mm mesh sieve, whereupon 2 parts of solid BDBP-TBA remained on the sieve. This aqueous dispersion was filtered, rinsed with approximately the same weight of water as the BDBP-TBA, and dried at 70° C. for 24 hours to provide 197 parts of a BDBP-TBA powder. This powder had a melting point of 104° C.

EXAMPLE 2

The same apparatus as used in Example 1 was charged with 200 parts of BDBP-TBA of 92% purity having a melting point of 45° C. and 200 parts of chloroform and the starting compound was thoroughly dissolved. The apparatus was further charged with 200 parts of water, 5 parts of nonylphenol ethoxylate (an average of 22 mols of EO added) phosphate and, as a crystal nucleus, 2 parts of a BDBP-TBA powder having a melting point of 114° C. With the stirrer driven at 300 rpm and the temperature maintained at 55° C., chloroform was recovered by distillation under reduced pressure. When the concentration of BDBP-TBA in the chloroform phase as calculated from the recovery rate of chloroform had reached 90%, crystallization took place giving rise to an aqueous dispersion, 100% of which passed a 1 mm mesh sieve. This dispersion was cooled, neutralized, filtered, rinsed and dried in the same manner as Example 1 to provide a powdery BDBP-TBA (199 parts) which had a melting point of 116° C.

EXAMPLE 3

The same apparatus as used in Example 1 was charged with 400 parts of a methylene chloride solution containing 50% of BDBP-TBA of 93% purity (containing 200 parts of BDBP-TBA) as obtained by brominating 2,2-bis(4'-allyl-3', 5'-dibromophenyl)propane using methylene chloride as the reaction solvent. The apparatus was further charged with 100 parts of water, 1 part of distyrenated phenol ethoxylate (an average of 8 mols of EO added) phosphate, 3 parts of oleyl alcohol ethoxylate (containing an average of 57% of polyoxyethylene) and 0.1 part of a BDBP-TBA powder having a melting point of 114° C. With the stirrer driven at 300 rpm, the temperature was increased for distillative recovery of methylene chloride. When the temperature had reached 60° C., the concentration of BDBP-TBA in the methylene chloride phase as calculated from the recovery rate of methylene chloride was 88% and the contents had become a viscous paste. When 100 parts of water at 20° C. was added, crystallization took place and, at the same time, the viscosity of the contents decreased giving rise to an aqueous dispersion. As this aqueous dispersion was further heated at 75° C. to remove the methylene chloride, the recovery rate of methylene chloride reached 98%. The dispersion was then cooled to 25° C., neutralized with sodium hydroxide, and passed through a 1 mm mesh sieve. As a result, 100% of the dispersion passed through the sieve. This dispersion was further filtered, rinsed and dried to provide a dry powder of BDBP-TBA (200 parts), the melting point of which was 118° C.

EXAMPLES 4–13

The same apparatus as used in Example 1 was charged with 400 parts of a methylene chloride solution containing 50% of a BDBP-TBA composition of 90% purity, water, 5 parts of a BDBP-TBA powder having a melting point of 114° C., and a surfactant and the methylene chloride was recovered by distillation at atmospheric pressure. The temperature at which crystallization took place, the concentration of BDBP-TBA in methylene chloride phase as calculated from the recovery rate of methylene chloride, the amount of solid BDBP-TBA which remained on the 1 mm mesh sieve, and the melting point of the powdery BDBP-TBA obtained after the same after-treatment of the aqueous dispersion as described in Example 1 are shown in Tables 1 and 2.

TABLE 1

| | Example 4 | Example 5 | Example 6 | Example 7 | Example 8 | Example 9 |
|---|---|---|---|---|---|---|
| Acidic phosphoric ester surfactant | 2-Ethylhexanol phosphate | Distyrenated phenol ethoxylate (EO 8 mols) phosphate | Dinonyl-phenol ethoxylate (EO 7 mols) phosphate | Lauryl alcohol ethoxylate (EO 20 mols) phosphate | Coconut alcohol phosphate | Distyrenated phenol ethoxylate (EO 8 mols) phosphate |
| Amount (parts) | 1.0 | 0.2 | 2.0 | 1.0 | 0.6 | 0.1 |
| Concomitant surfactant | Nonylphenol ethoxylate (EO 60%) | — | Softanol 70 (EO 58%) | Octylphenol ethoxylate (EO 7 mols) sulfate ammonium salt | 2-Ethylhexanol ethoxylate (EO 20 mols) sulfomono-succinate 2Na | — |
| Amount (parts) | 2.0 | — | 1.0 | 1.0 | 1.0 | — |
| Water initially added (parts) | 100 | 100 | 140 | 60 | 180 | 100 |
| Water supplementally added (parts) | 100 | 60 | 60 | 240 | — | 100 |
| Timing of supplemental addition | At 90% concentration of BDBP-TBA | At 91% concentration of BDBP-TBA | After crystallization | At 90% concentration of BDBP-TBA | — | At 90% concentration of BDBP-TBA |
| Concentration of BDBP-TBA (%) at crystallization | 90 | 92 | 90 | 90 | 90 | 90 |
| Temperature (°C.) at crystallization | 56 | 57 | 57 | 55 | 60 | 59 |
| State of dispersion | Good | Good | Good | Good | Dispersed but particle diameter somewhat large | Dispersed but particle diameter somewhat large |
| On 1 mm mesh sieve (parts) | 3 | 0 | 0 | 2 | 7 | 20 |
| Melting point (°C.) of dried product | 114 | 115 | 115 | 114 | 114 | 114 |

Note 1: "Parts" in this table represent parts by weight relative to 200 parts of BDBP-TBA.
Note 2: The "concentration of BDBP-TBA at crystallization" was calculated from the initial amount of methylene chloride and the recovered amount of methylene chloride.
Note 3: The "on 1 mm mesh sieve" was determined by sieving the aqueous dispersion with a 1 mm mesh sieve, rinsing the residue on the sieve, drying it and recording its weight.
Note 4: As regards the "melting point of dried product", the aqueous dispersion was neutralized, filtered, rinsed with 200 parts of water, and dried at 70° C. for 24 hrs and its melting point was determined with an automatic melting point measuring instrument.

TABLE 2

|  | Example 10 | Example 11 | Example 12 | Example 13 |
|---|---|---|---|---|
| Surfactant | Cetylpyridinium chloride | Sodium palmitate | Sodium lauryl benzene-sulfonate | Distyrenated phenol ethoxylate (EO 8 mols) phosphate, neutralized with Na |
| Amount (parts) | 1.0 | 0.4 | 0.2 | 1.0 |
| Surfactant | Dinonylphenol ethoxylate (EO 60%) | — | Dobanol 25 ethoxylate (EO 70%) | — |
| Amount (parts) | 1.0 | — | 8.0 | — |
| Water initially added (parts) | 100 | 160 | 140 | 120 |
| Water supplementally added (parts) | 80 | — | 60 | — |
| Timing of supplemental addition | At 90% concentration of BDBP-TBA | — | After crystallization | — |
| Concentration of BDBP-TBA (%) at crystallization | 90 | 89 | 90 | 93 |
| Temperature (°C.) at crystallization | 56 | 60 | 57 | 60 |
| State of dispersion | Good | Dispersed but particle diameter somewhat large | Dispersed but particle diameter somewhat large | Dispersed but particle diameter somewhat large |
| On 1 mm mesh sieve (parts) | 8 | 15 | 20 | 24 |
| Melting point (°C.) of dried product | 114 | 114 | 115 | 113 |

Note 1: "Parts" in this table represent parts by weight relative to 200 parts of BDBP-TBA.
Note 2: The "concentration of BDBP-TBA at crystallization" was calculated from the initial amount of methylene chloride and the recovered amount of methylene chloride.
Note 3: The "on 1 mm mesh sieve" was determined by sieving the aqueous dispersion with a 1 mm mesh sieve, rinsing the residue on the sieve, drying it and recording its weight.
Note 4: As regards the "melting point of dried product", the aqueous dispersion was filtered, rinsed with 200 parts of water, and dried at 70° C. for 24 hrs and its melting point was determined with an automatic melting point measuring instrument.

EXAMPLE 14

The procedure of Example 3 was repeated except that 0.01 part of antimony trioxide with a mean particle diameter of 0.8–1.5 microns was used in lieu of 0.1 part of BDBP-TBA powder as the crystal nucleus. The procedure yielded an aqueous dispersion, 96% of which passed a 1 mm mesh sieve. The melting point of the filtered, rinsed and dried BDBP-TBA powder (192 parts) was 118° C.

EXAMPLE 15

The same apparatus as used in Example 1 was charged with 500 parts of a homogeneous 40% BDBP-TBA solution containing BDBP-TBA of 92% purity (containing 200 parts of BDBP-TBA composition) as obtained by bromination of 2,2-bis(4'-allyl-3',5'-dibromophenyl)-propane using carbon tetrachloride as the reaction solvent. The apparatus was further charged with 160 parts of water and 2 parts of octylphenol ethoxylate (an average of 7 mols of EO added) phosphate, and with the stirrer driven at 300 rpm, the temperature was increased for distillative recovery of carbon tetrachloride at atmospheric pressure. When the concentration of BDBP-TBA in carbon tetrachloride phase as calculated from the recovery rate of carbon tetrachloride had reached 85% at an internal temperature of 96° C., heating was discontinued. The contents at this stage were a viscous paste. After 1 part of a BDBP-TBA powder having a melting point of 114° C. was added, the temperature was lowered to 75° C., whereupon crystallization took place and the viscosity of the system decreased, giving rise to an aqueous dispersion. This aqueous dispersion was distilled under reduced pressure at 70°–75° C. for further recovery of the organic solvent. The final recovery rate of carbon tetrachloride was 98%. The dispersion was then cooled to 25° C. and neutralized with sodium hydroxide. The aqueous dispersion thus obtained passed a 1 mm mesh sieve 100% and the BDBP-TBA powder (198 parts) obtained after filtration, rinse and drying had a melting point of 116° C.

COMPARATIVE EXAMPLE 1

The same BDBP-TBA of 93% purity as used in Example 3 was dissolved in methylene chloride and the solution was concentrated under reduced pressure up to a temperature of 57° C. until the volatile content reached 1%. However, the solution remained a viscous liquid, failing to yield a solid. When it was cooled to 25° C., a resinous solid was obtained but its melting point was 45° C.

COMPARATIVE EXAMPLE 2

The procedure of Example 1 was repeated except that the surfactant (1 part of nonylphenol ethoxylate (an average of 9 mols of EO added) phosphate) was omitted from the charge. Though the methylene chloride was distilled off and recovered, with the BDBP-TBA-containing methylene chloride and water still forming distinct phases, deposits were formed on the flask wall and stirrer blade as the BDBP-TBA concentration and the system viscosity increased progressively so that no emulsification/dispersion could be achieved at all. Moreover, although concentration further continued until the concentration of BDBP-TBA in methylene chloride as calculated from the recovery rate of methylene chloride reached 94%, no crystallization could be obtained. When the system was cooled to 20° C., the deposits on the glass wall and stirrer blade solidified into resinous masses. The melting point of the masses was 44° C.

COMPARATIVE EXAMPLE 3

The procedure of Example 3 was repeated except that no crystal nucleus was added. When the concentration of BDBP-TBA in methylene chloride as calculated from the recovery rate of methylene chloride reached 87% and the temperature was 57° C., the viscous liquid underwent phase inversion to a low-viscosity oil-in-water emulsion. As this system was further heated, a further amount of methylene chloride was distillatively recovered but the rate of recovery was low and the recovery yield at an internal temperature of 80° C. was corresponding to a BDBP-TBA concentration of 90%. At this stage, BDBP-TBA in the emulsion had not formed crystals. Then, as this oil-in-water emulsion was cooled gradually at a rate of 10° C./hour, the BDBP-TBA particles conglomerated to form a paste-like mass at 50° C.

What is claimed is:

1. A method of producing a high-melting powder of 2,2-bis[4'-(2",3"-dibromopropoxy)-3',5'-dibromophenyl]propane characterized by comprising a step of adding water to a solution of 2,2-bis[4'-(2",3"-dibromopropoxy)-3',5'-dibromophenyl]propane in an organic solvent in the presence of a surfactant to give a water-in-oil emulsion and a step of removing the organic solvent from said emulsion in the presence of a crystal nucleus to induce crystallization to give an aqueous dispersion of 2,2-bis[4'-(2",3"-dibromopropoxy)-3',5'-dibromophenyl]propane.

2. The method according to claim 1 wherein said surfactant is an acidic phosphoric ester type surfactant.

3. The method according to claim 1 or 2 wherein said crystallization is induced at a temperature of not over 80° C.

4. A powder of 2,2-bis[4'-(2",3"-dibromopropoxy)-3',5'-dibromophenyl]propane having a melting point of not less than 100° C. as obtained by the method claimed in claim 1 or 2.

5. The method of claim 1, wherein the amount of surfactant is at least 0.05 wt. % relative to the amount of 2,2-bis[4'-(2",3"-dibromopropoxy)-3',5'-dibromophenyl]-propane and the amount of water is 20–100 wt. % relative to the amount of 2,2-bis[4'-(2",3"-dibromopropoxy)-3',5'-dibromophenyl]-propane.

* * * * *